United States Patent
Baker et al.

[11] Patent Number: 5,962,659
[45] Date of Patent: Oct. 5, 1999

[54] ANTHELMINTIC MILBEMYCINS AND AVERMECTINS

[75] Inventors: Geoffrey Harold Baker; Roderick John Dorgan; David Owen Morgan, all of Epsom; Peter Robin Shelley, Betchworth; Simon Edward Blanchflower, Tadworth, all of United Kingdom

[73] Assignee: Pfizer, Inc., New York, N.Y.

[21] Appl. No.: 07/798,971

[22] Filed: Nov. 29, 1991

Related U.S. Application Data

[63] Continuation of application No. 07/525,094, May 17, 1990, abandoned.

[30] Foreign Application Priority Data

May 17, 1989 [GB] United Kingdom ............ 8911281
Dec. 22, 1989 [GB] United Kingdom ............ 8929041

[51] Int. Cl.[6] ............................................. C07H 1/00
[52] U.S. Cl. .................. 536/7.1; 536/18.5; 536/18.6; 549/264
[58] Field of Search ................... 536/18.5, 18.6, 536/7.1; 549/269

[56] References Cited

U.S. PATENT DOCUMENTS 4,408,059 10/1983 Smith, III et al. .................... 549/214

*Primary Examiner*—Elli Peselev
*Attorney, Agent, or Firm*—Hopgood, Calimafde, Kalil & Judlowe

[57] ABSTRACT

Novel compounds of formula (I):

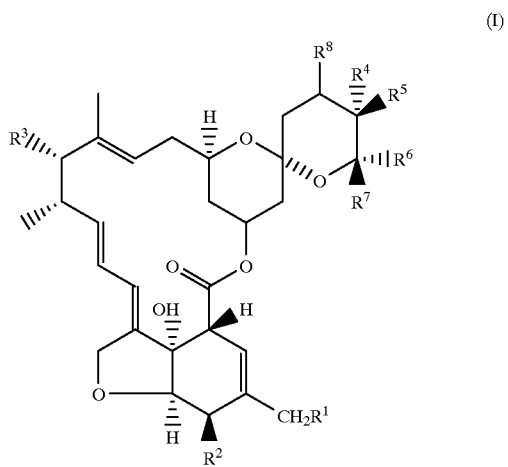

wherein $R^1$ is hydrogen or optionally protected hydroxy; $R^2$ is alkoxy, optionally protected hydroxy, oxo or optionally O-substituted oximino; $R^3$ is hydrogen, optionally protected hydroxy, or a group 4'-(α-L-oleandrosyl)-α-L-oleandrosyloxy or α-L-oleandrosyloxy wherein the terminal hydroxy group is optionally protected; $R^4$, $R^5$, $R^6$ and $R^7$ are the same or different and each is hydrogen or an organic radical; and $R^8$ is an optionally substituted amino or imino group such as optionally O-substituted oxyimino, optionally N-substituted hydrazone, or optionally N-substituted semicarbazone; are useful in the treatment of helminthiasis in humans and animals.

5 Claims, No Drawings

ANTHELMINTIC MILBEMYCINS AND AVERMECTINS

This application is a continuation of application Ser. No. 525,094, filed May 17, 1990, now abandoned.

The present invention relates to novel anthelmintic compounds, to processes for their production, to pharmaceutical formulations containing them, and to their use in human or veterinary medicine.

The milbemycins and avermectins are a group of macrolide antibiotics which have been prepared by the cultivation of microorganisms and are described in inter alia GB-A-1,390,336, J. Antibiotics 29(3), 76-14 to 76-16 and 29 (6), 76-35 to 76-42, GB-A-2 170 499, EP-A-O 073 660 and EP-A-0 204 421. They have anthelmintic activity. Further anthelmintically active milbemycins and avermectins are described in GB-A-2 176 180, EP-A-0 212 867, EP-A-0 237 339, EP-A-0 241 146, EP-A-0 214 731, EP-A-0 194 125, EP-A-0 170,006, and U.S. Pat. No. 4,285,963.

The compounds disclosed in the above references include compounds of formula (A):

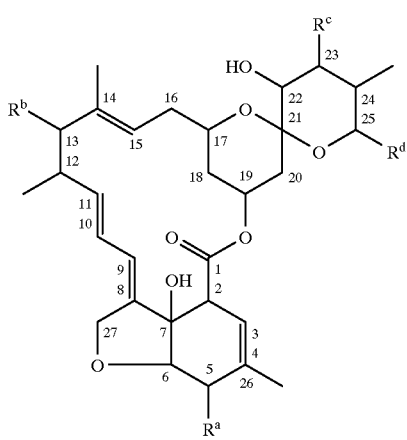

(A)

wherein $R^a$ is methoxy or hydroxy, $R^b$ is hydrogen, $R^c$ is hydrogen, pentanoyloxy, heptanoyloxy, or 2-methylhexanoyloxy, and $R^d$ is methyl or ethyl, with the proviso that when $R^c$ is hydrogen, $R^a$ is methoxy; or $R^a$ is methoxy or hydroxy, $R^b$ is hydrogen, $R^c$ is 2-methylbutanoyloxy, 2,4-dimethylpent-2-enoyloxy, or 2,4-dimethylpentanoyloxy, and $R^d$ is methyl or ethyl, with the proviso that when $R^d$ is ethyl, $R^a$ is hydroxy and $R^c$ is 2,4-dimethylpentanoyloxy; or $R^a$ is methoxy or hydroxy, $R^b$ is the group of formula:

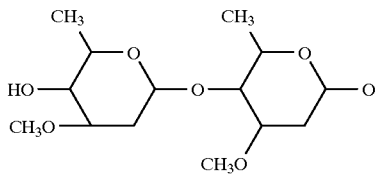

(4'-(α-L-oleandrosyl)-α-L-oleandrosyloxy), $R^c$ is hydroxy, and $R^d$ is 1-methyl propyl.

EP-A-O 254 583 (U.S. Ser. No. 076,274) describes compounds of formula (B):

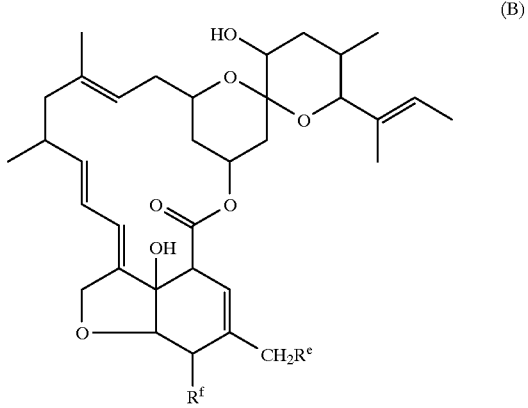

(B)

wherein $R^e$ is hydrogen or E 2-methyl 2-butenoyloxy, and $R^f$ is methoxy or hydroxy, with the proviso that when $R^e$ is E 2-methyl 2-butenoyloxy, $R^f$ is methoxy.

EP-A-0325462 (U.S. Ser. No. 299,933) describes compounds of formula (C):

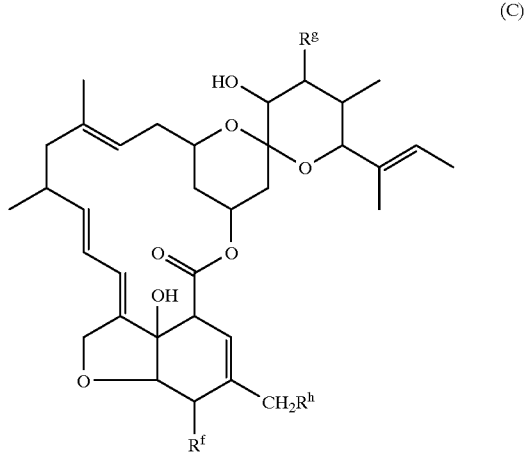

(C)

wherein $R^g$ and $R^h$ are as set out in the following table:

| Compound | $R^g$ | $R^h$ |
| --- | --- | --- |
| VM48130 | O—CO—CH(CH$_3$)$_2$ | H |
| VM48633 | H | O—CO—CH=C(CH$_3$)$_2$ |
| VM47704 | H | O—CO—CH$_2$—CH(CH$_3$)$_2$ |
| VM48642 | H | O—CO—CH$_2$—furyl |

EP-A-0 288 205 (U.S. Ser. No. 183,581) discloses compounds of formula (D):

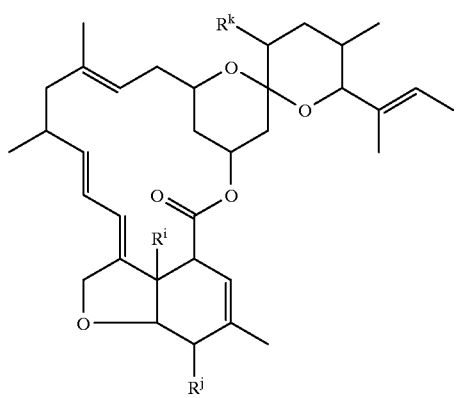

(D)

wherein $R^i$ is hydroxy or methoxy and $R^j$ and $R^k$ are the same or different and each is selected from optionally protected hydroxy, alkoxy, acyloxy, sulphonyloxy, oxo and optionally O-substituted oximino.

EP-A-0 259 779, EP-A-0 293 549, EP-A-0 307 225 and GB-A-2192630 describe compounds of formula (E):

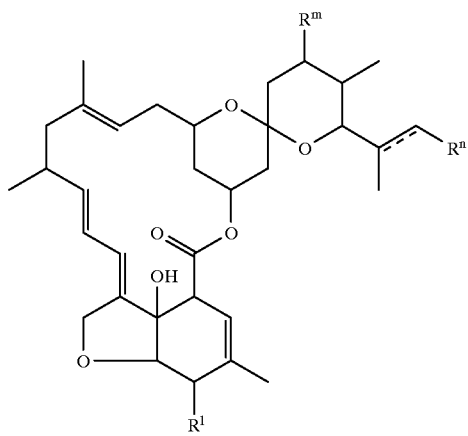

(E)

wherein $R^l$ is optionally protected hydroxy or methoxy, $R^m$ is optionally protected hydroxy, oxo, or an imino group such as optionally O-substituted oxyimino, optionally N-substituted hydrazone, or optionally N-substituted semicarbazone, $R^n$ is methyl, ethyl or isopropyl, and the dashed line is a double bond or an epoxide group.

EP-A-0 260 536 and EP-A-0 260 537 describe compounds of formula (F):

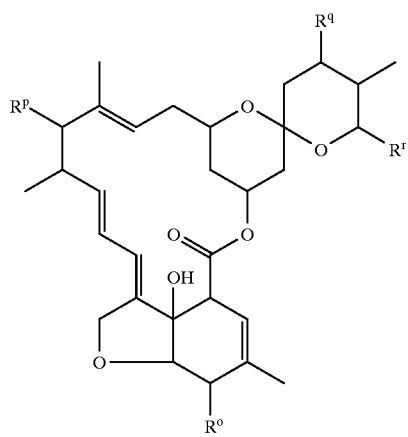

(F)

wherein $R^o$ is optionally protected hydroxy or methoxy, $R^p$ is hydrogen or a sugar residue, $R^q$ is optionally protected hydroxy, oxo, or an imino group such as optionally O-substituted oxyimino or optionally N-substituted hydrazone, and $R^r$ is isopropyl or sec-butyl.

The absolute configuration of the compounds of formulae (A) to (F) is believed to be as follows:

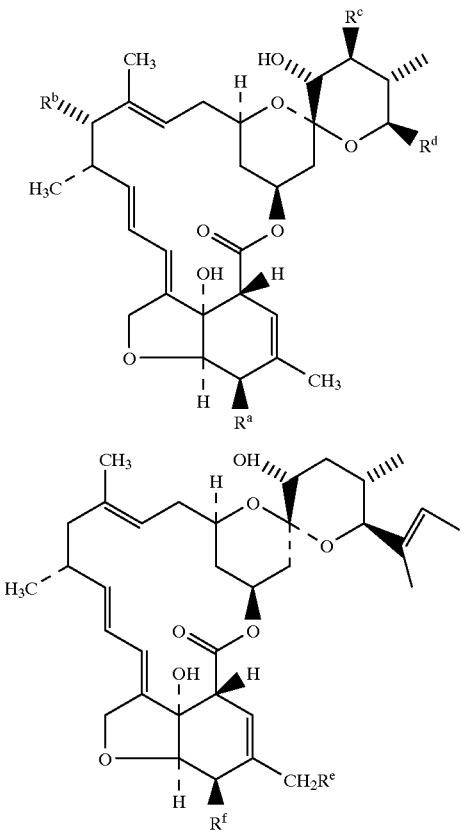

-continued

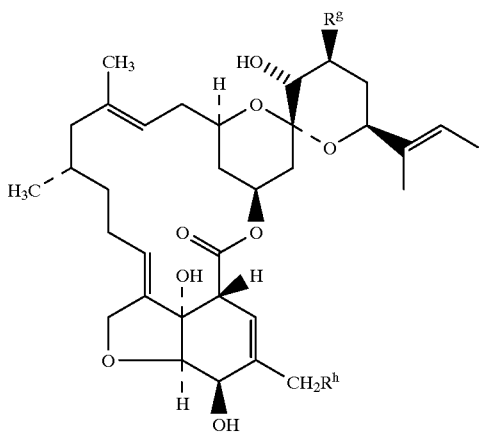

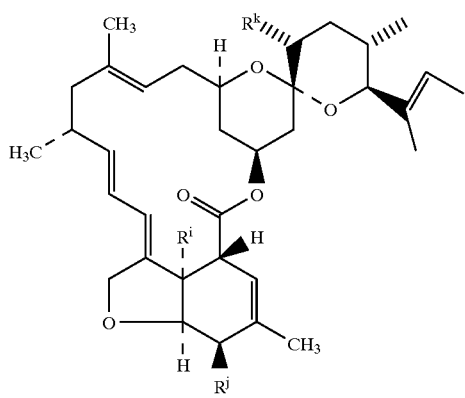

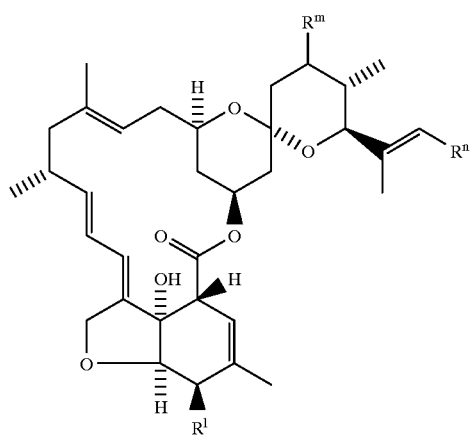

-continued

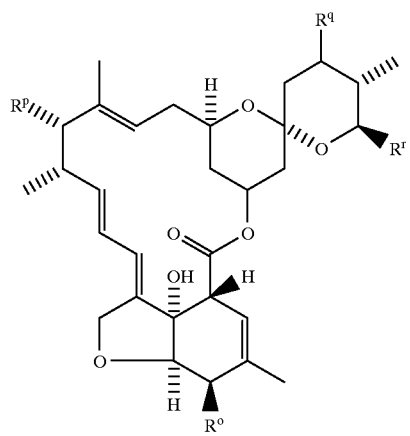

We have now discovered that it is possible to prepare novel compounds from starting materials having a hydroxy substituent at the c-22 position, such as compounds of formulae (A) to (D) above and the compounds disclosed in EP-A-O 334 484, and that these compounds are useful as anthelmintically active compounds.

According to the present invention there is provided a compound or formula (I);

(I)

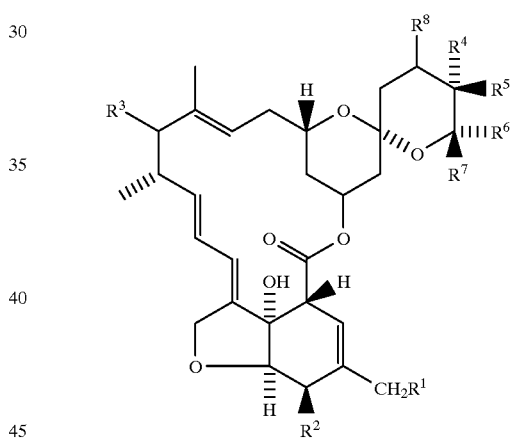

wherein $R^1$ is hydrogen or optionally protected hydroxy; $R^2$ is alkoxy, optionally protected hydroxy, oxo or optionally O-substituted oximino; $R^3$ is hydrogen, optionally protected hydroxy, or a group 4'-(α-L-oleandrosyl)-α-L-oleandrosyloxy or α-L-oleandrosyloxy wherein the terminal hydroxy group is optionally protected; $R^4$, $R^5$, $R^6$ and $R^7$ are the same or different and each is hydrogen or an organic radical; and $R^8$ is an optionally substituted amino or imino group such as optionally O-substituted oxyimino, optionally N-substituted hydrazone, or optionally N-substituted semicarbazone; with the proviso that the compound of formula (I) is not a compound of formula (E) or (F) above or a compound disclosed In EF-A-0 307 220. Typically $R^3$ is in the α-configuration shown above for formulae (A) and (F). When $R^3$ is in the β-configuration then it is preferably optionally protected hydroxy, and/or $R^1$ is preferably hydrogen, and/or $R^2$ is preferably methoxy or optionally protected hydroxy.

Preferably, (a) when $R^1$ is optionally protected hydroxy, $R^3$ is hydrogen, and/or (b) when $R^4$ is methyl and $R^5$ and $R^6$ are hydrogen, $R^7$ does not have any of the values set out in Table 1 hereinbelow, and/or (c) when $R^4$ is methyl and $R^5$ and $R^6$ are hydrogen, $R^7$ does not have any of the values set out in Table II hereinbelow, and/or (d) when $R^2$ is not methoxy or optionally protected hydroxy, $R^1$ and $R^3$ are both hydrogen.

Certain compounds of formula (I) wherein $R^8$ is optionally protected hydroxy or oxo are also novel, and such compounds form a further aspect of the invention.

Thus, a particular aspect or the invention provides a compound of formula (I) as defined hereinabove wherein $R^8$ is optionally protected by hydroxy or oxo, with the proviso that (a) when $R^3$, $R^5$ and $R^6$ are hydrogen and $R^4$ is methyl, then $R^7$ does not have any of the values set out in Table III hereinbelow, (b) when $R^3$ is not hydrogen, $R^4$ is methyl and $R^5$ and $R^6$ are hydrogen, then $R^7$ does not have any of the values set out in Table IV hereinbelow, (c) when $R^3$, $R^5$ and $R^6$ are hydrogen and $R^4$ is ethyl, then $R^7$ is not (z)-4-methylpent-2-en-2-yl, and (d) when $R^3$ is not hydrogen, $R^4$ is methyl, and $R^5$ is hydrogen, the 25-position is not substituted in the same way as that of compound III of U.S. Pat. No. 4,285,963, and (e) it is not a compound disclosed in EP-A-0 317 148, EP-A-0 307 220, EP-A-O 308 145, EP-A-O 350 187 or EP-A-O 335 541.

TABLE I

—CH(CH$_3$)$_2$, —CH(CH$_3$)C$_2$H$_5$

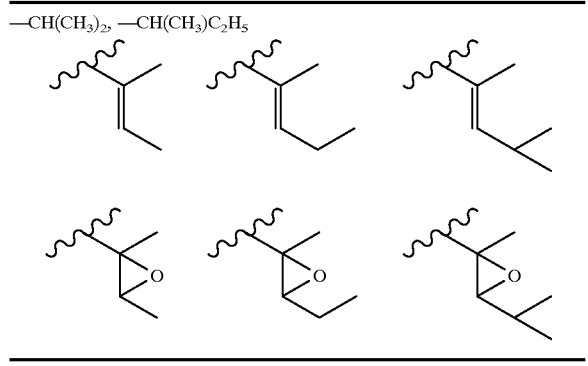

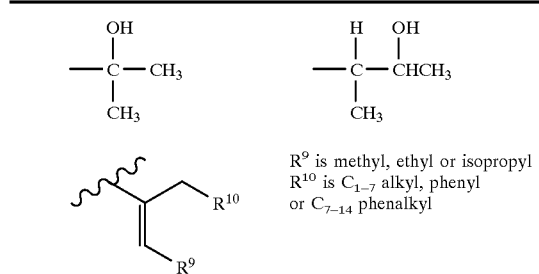

TABLE II

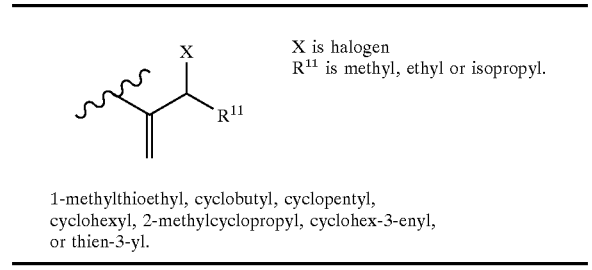

TABLE II-continued

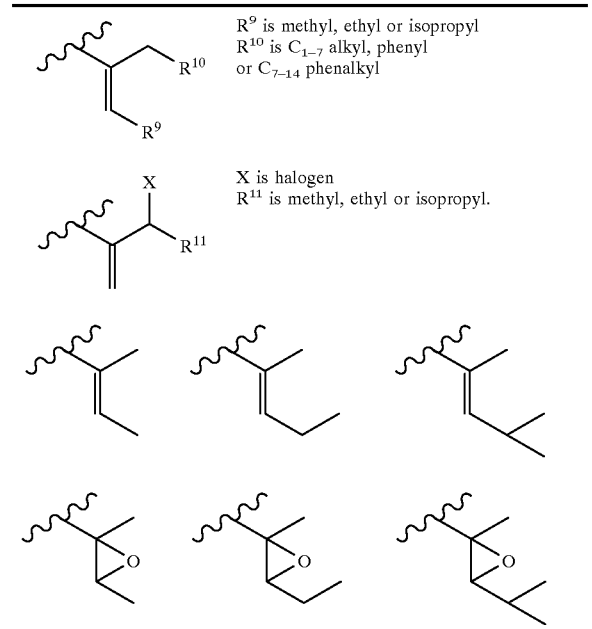

1-methylthioethyl, cyclobutyl, cyclopentyl, cyclohexyl, 2-methylcyclopropyl, cyclohex-3-enyl, or thien-3-yl.

TABLE III

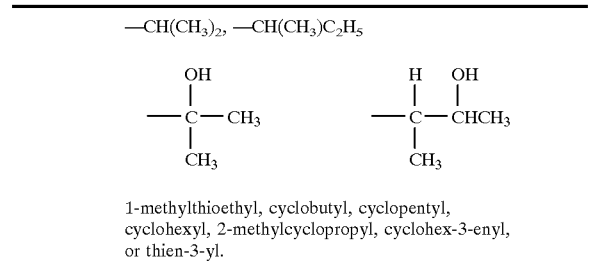

TABLE IV

—CH(CH$_3$)$_2$, —CH(CH$_3$)C$_2$H$_5$

|  OH |  |  H OH |
| --- | --- | --- |
| —C—CH$_3$ |  | —C—CHCH$_3$ |
|  CH$_3$ |  |  CH$_3$ |

1-methylthioethyl, cyclobutyl, cyclopentyl, cyclohexyl, 2-methylcyclopropyl, cyclohex-3-enyl, or thien-3-yl.

Preferably, when $R^4$ is methyl and $R^5$ and $R^6$ are hydrogen, $R^7$ is not a group:

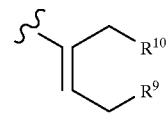

wherein $R^9$ is methyl, ethyl or isopropyl and $R^{10}$ is alkyl, phenalkyl or phenyl.

It is also preferred that, when $R^4$ is methyl and $R^5$ and $R^6$ are hydrogen, $R^7$ is not selected from the group consisting of pent-2-yl, 3-methylbut-2-yl, hex-2-yl, pent-4-en-2-yl, 1-cyclopropylethyl, cycloheptyl, 4,4-difluorocyclohexyl, 4-methylenecyclohexyl, 3-methylcyclohexyl, cyclopenten-1-yl, cyclohexen-1-yl, tetrahydropyran-4-yl, thien-2-yl, 3-furyl, and 2-chlorothien-4-yl.

In a particular aspect, when $R^4$ is methyl and $R^5$ and $R^6$ are hydrogen, $R^7$ is not an alpha-branched $C_{3-8}$ alkylthioalkyl group; a $C_{3-8}$ cycloalkyl group optionally substituted by one $C_{1-4}$ alkyl group; a $C_{5-8}$ cycloalkenyl group; or a 3 to 6 membered sulphur containing heterocyclic ring. More especially, $R^7$ is not an alpha-branched $C_{3-8}$ alkyl, alkenyl or alkylthioalkyl group; a $C_{5-8}$ cycloalkylalkyl group wherein the alkyl group is an alpha-branched $C_{2-5}$ alkyl group; a $C_{3-8}$ cycloalkyl group optionally substituted by methylene or one or more $C_{1-4}$ alkyl groups or halo atoms; a $C_{5-8}$ cycloalkenyl group; or a 3 to 6 membered oxygen or sulphur containing heterocyclic ring which may optionally be substituted by one or more halo atoms.

In a still further particular aspect, when $R^4$ is methyl and $R^5$ and $R^6$ are hydrogen, $R^7$ is not an alpha-branched $C_3$–$C_8$ alkyl, alkenyl, alkynyl, alkoxyalkyl or alkylthioalkyl group; a $C_5$–$C_8$ cycloalkylalkyl group wherein the alkyl group is an alpha-branched $C_{2-5}$ alkyl group; a $C_3$–$C_8$ cycloalkyl or $C_{5-8}$ cycloalkenyl group, either of which may optionally be substituted by methylene or one or more $C_1$–$C_4$ alkyl groups or halo atoms; or a 3 to 6 membered oxygen or sulphur containing heterocyclic ring which may be saturated, or fully or partially unsaturated and which may optionally be substituted by one or more $C_1$–$C_4$ alkyl groups or halo atoms. More especially, $R^7$ is not an alpha-branched alkyl, alkenyl, alkynyl, alkoxyalkyl or alkylthioalkyl group; a cycloalkylalkyl group wherein the alkyl group is alpha-branched; a cycloalkyl or cycloalkenyl group, either of which may optionally be substituted by methylene or one or more alkyl groups or halo atoms; or an oxygen or sulphur containing heterocyclic ring which may be saturated, or fully or partially unsaturated and which may optionally be substituted by one or more alkyl groups or halo atoms.

According to a further preferred aspect, when $R^4$ is ethyl and $R^5$ and $R^6$ are hydrogen, $R^7$ is not (z)-4-methyl-pent-2-en-2-yl.

According to a still further preferred aspect, when $R^4$ is methyl and $R^5$ is hydrogen, the 25-position is not substituted in the same way as that of compound III of U.S. Pat. No. 4,285,963.

Suitable protecting groups for hydroxy include TBDMS (t-butyldimethylsilyl), and acyl. Further suitable protecting groups are described in, for example, "Protective Groups In organic synthesis" Theodore W. Greens, Wiley-Interscience 1981 Ch 2, 10–86.

When any of $R^4$ to $R^7$ is an organic radical it may advantageously be selected from the group consisting of alkyl, alkenyl, alkynyl, aryl, heterocyclyl, mono-, bi- and tri-cycloalkyl, mono-, bi- and tri-cycloalkenyl and aralkyl.

As used herein alkyl includes straight and branched $C_{1-20}$, more especially $C_{1-12}$, particularly $C_{1-6}$ alkyl, and alkenyl and alkynyl include straight and branched $C_{2-20}$, more especially $C_{2-12}$, particularly $C_{2-6}$ alkenyl and alkynyl.

When any of $R^4$ to $R^7$ comprises an alkyl, alkenyl or alkynyl moiety that moiety nay optionally be substituted by one or more substituents selected from the group consisting of hydroxy, alkoxy, alkylthio, oxo, halogen, trifluoromethyl, and optionally substituted amino.

When used herein the term 'aryl' includes phenyl and naphthyl optionally substituted with up to five, preferably up to three, groups selected from halogen, $C_{1-6}$ alkyl, aryl, $C_{1-6}$ alkoxy, halo substituted ($C_{1-6}$) alkyl, hydroxy, amino, nitro, carboxy, $C_{1-6}$ alkoxycarbonyl, $C_{1-6}$ alkoxycarbonyl-($C_{1-6}$)-alkyl, $C_{1-6}$ alkylcarbonyloxy, or $C_{1-6}$ alkylcarbonyl groups.

The term 'heterocyclyl' includes saturated, unsaturated and aromatic single or fused rings comprising up to four hetero atoms in the ring selected from oxygen, nitrogen and sulphur and optionally substituted with up to three halogen, $C_{1-6}$ alkyl, $C_{1-6}$ alkoxy, halo-($C_{1-6}$)-alkyl hydroxy, amino, carboxy, $C_{1-6}$ alkoxycarbonyl, $C_{1-6}$ alkoxycarbonyl($C_{1-6}$) alkyl, aryl or oxo groups.

Suitably the heterocyclic ring comprise from 4 to 7 ring atoms, preferably 5 to 6 atoms.

The term 'halogen' refers to fluorine, chlorine, bromine and iodine.

Particularly suitable substituents for an amino or imino group such as an oxime, hydrazone or semicarbazone group include one or more organic radicals as defined hereinabove for $R^4$ to $R^7$, for example the substituents set out in EP-A-0 288 205, EF-A-0 259 779, EP-A-0 260 537, EP-A-0 260 536, GB-A-2 192 630, and EP-A-0 307 225.

Those skilled in the art will appreciate that an N-substituted imino group such as an oxime may exist as either an E or Z isomer, or as a mixture of E and Z isomers, and that an E or Z isomer may be converted to the other isomer or to a mixture of isomers by standard techniques such as acid treatment.

As used herein mono-, bi- and tri-cycloalkyl include $C_{3-20}$, especially $C_{3-12}$, more especially $C_{4-8}$, groups, and mono-, bi.- and tri-cycloalkenyl include $C_{4-20}$, especially $C_{4-12}$, more especially $C_{5-8}$ groups. When any of $R^4$ to $R_7$ comprises a mono-, bi- or tri-cycloalkyl or mono-, bi- or tri-cycloalkenyl moiety, that moiety may be substituted as set out above for alkyl, alkenyl, and alkynyl, and/or by one or more substituents selected from the group consisting of methylene and alkyl. Bicyclic and tricyclic groups may be fused or bridged and are preferably attached via a carbon atom which is common to two rings.

Any two of $R^4$ to $R^7$ may be taken together with the carbon atom(s) to which they are attached to designate a cycloalkyl, cycloalkenyl, aryl or heterocyclyl group which may optionally be substituted as set out above.

In a preferred aspect of the invention, $R^1$ is hydrogen, $R^2$ is methoxy or hydroxy, and $R^3$ is hydrogen.

In a particular aspect of the invention, $R^5$ and $R^6$ are hydrogen, one of $R^4$ and $R^7$ is hydrogen or alkyl, such as methyl, and the other of $R^4$ and $R^7$ is an organic radical, more especially an aryl, cycloalkyl, alkenyl, cycloalkenyl or alkyl group.

Preferably, $R^2$ is a hydroxy group.

The compound or mixture of compounds according to the invention is suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

The compounds of the invention have parasiticidal properties, for example against nematodes such as *Trichostrongylus colubriformis*, and are useful for the treatment of helminthiasis in animals such as mammals, including humans and domesticated animals (including farm animals).

Accordingly the present invention also provides a compound according to the invention, for use in the treatment of the human or animal body, especially for treating endo- and ectoparasitic infestations and particularly for treating helminthiasis of domestic and farm animals.

The term helminthiasis encompasses those diseases of man and animals caused by infestation with parasitic worms such as Strongyles, Ascarids, hookworms lungworms, filarial worms and whipworms. The compound may also be used against nematodes occurring in the soil or parasitic to plants.

The compounds of the invention are also active against Arthropods. The phylum Arthropoda comprises insects— such as biting flies, lice, bugs, beetles and fleas—and arachnids—such as mites and ticks.

Thus, a broad aspect of the invention provides a method of eradicating arthropod or nematode infestations, which method comprises applying a compound according to the invention or a derivative thereof to the arthropods or nematodes or to their environment.

The present invention thus provides a pesticidal composition comprising a compound according to the invention or a derivative thereof together with a a suitable carrier or excipient, such as an aerosol formulation.

The present invention also provides a pharmaceutical or veterinary composition comprising a compound according to the invention or a pharmaceutically acceptable derivative thereof together with a pharmaceutically or veterinarily acceptable carrier or excipient.

The present invention also provides a method of treatment or prophylaxis of endo- and ectoparasitic infestations, especially helminthiasis, of animals (including birds and fish), especially humans and domesticated mammals, which comprises administering an effective non-toxic amount of a compound according to the invention or a pharmaceutically acceptable derivative thereof, or a composition according to the invention, to a patient in need thereof.

The composition according to the invention may be formulated for administration in any convenient way for use in human or veterinary medicine, by analogy with other anthelmintics.

In suitable formulation: the drug may be administered to animals orally (as a paste, drench, bolus, capsule or tablet), parenterally, perculaneously, as a food additive (eg granules, pellets or powder), or may be prepared as an aerosol spray formulation.

The compounds of the invention may be formulated as a mixture with each other and/or with other anthelmintics, insecticides, acaricides or other pharmacologically active substances.

Suitably the composition consists of sufficient material to provide a dose of from 0.001 to 100 mg of active ingredient per kg of animal body weight per dose, more suitably 0.01 to 10 mg/kg per dose.

A composition according to the invention may suitably contain from 0.1% by weight, preferably from 1.0 to 60% by weight, of the compound according to the invention (based on the total weight of the composition), depending on the method of administration.

It will be appreciated that, in some cases, it will be advisable to repeat the dosing of the infected or potentially infected human or animal with the compound of the invention according to conventional dosage regimes used with anthelmintics.

Compounds of formula (I) wherein $R^8$ is an imino group may be prepared by reacting the corresponding 23 Keto derivative with an amino containing compound such as an amine, hydroxylamine, hydrazine or semicarbazide to yield derivatives of the type where $R^8$ is optionally substituted imino, oxyimino, hydrazone or semicarbazone, respectively.

Suitable processes are described in EP-A-0 259 779, EP-A-0 260 537, EP-A-0 260 536 and GB-A-2192630.

Compounds of formula (I) wherein $R^8$ is a substituted oxyimino group may be prepared by reacting the corresponding 23 hydroxyimino derivative with a suitable etherifying agent, for example an alkyl halide in the presence of a base such as triethylamine.

Furthermore, the 23-Keto derivative may be reduced to the alcohol using a suitable hydride reducing agent such as sodium borohydride, or L-selectride (Trade Mark Aldrich Chemical Co.).

A 23-imino derivative may be reduced to the corresponding amine using a suitable reducing agent such as sodium cyanoborohydride.

The 23-Keto derivative can be obtained by hydrating and cyclizing a compound of formula (II):

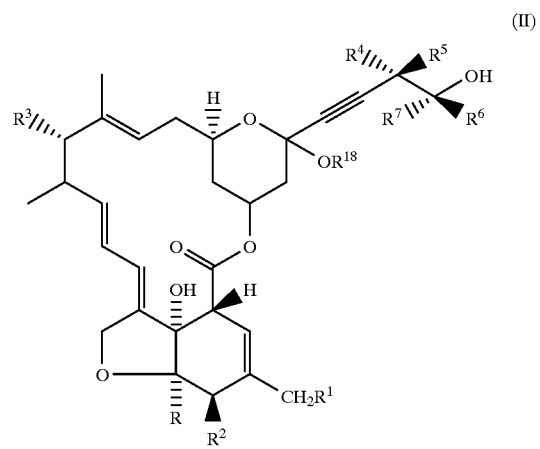

wherein $R^1$ to $R^7$ have the values set out above, and $R^{18}$ is hydrogen or lower alkyl, more particularly $C_{1-3}$ alkyl.

The acetylene (II) may be hydrated and cyclized to give the 23-Keto derivative by the action of an aqueous acid in the presence of a suitable mercury salt such as mercuric oxide. Other methods for the hydration of acetylenes are contained in standard texts e.g. The Chemistry of the C—C Triple Bond Ed S Patai Publ Wiley: New York and references cited therein.

The 23-keto derivative can also be obtained by cyclizing a compound of formula (V)

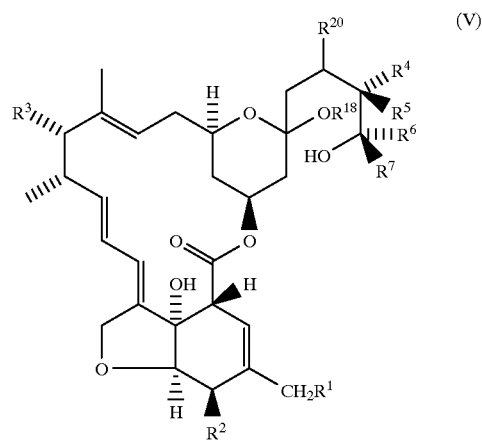

wherein $R^1$ to $R^7$ ano $R^{18}$ have the values set out above, and $R^{20}$ is an optionally protected ketone such as an acetal, for example by treatment with aqueous acid followed, if required by removal of any protecting group.

Alternatively, compounds of formula (I) wherein $R^8$ is oxo or substituted oxyimino may be prepared by cyclizing a compound of formula (IV):

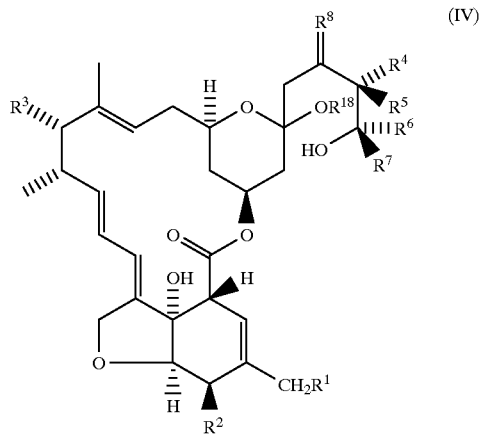

wherein $R^1$ to $R^8$ and $R^{18}$ have the values set out above, for example by treatment with aqueous acid.

It should be appreciated that the configuration at C21 of the compound of formula (I) will be subject to thermodynamic control (as discussed eg by P. Deslongchamps et al, Canadian J. Chem. [1981] 59, 1105): it is believed that the epimer in which the configuration at C21 is as in the naturally occurring compounds of formulae (A), (B) and (C) is normally thermodynamically favoured.

Compounds of formula (II), (IV) and (V) may be obtained from compounds of formula (III):

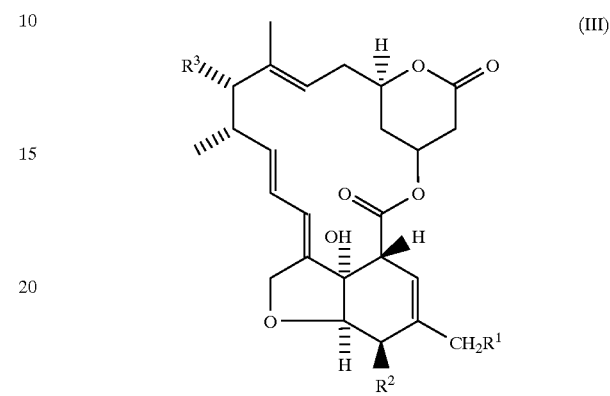

wherein $R^1$ to $R^3$ are as defined above, via the routes shown in Scheme I below:

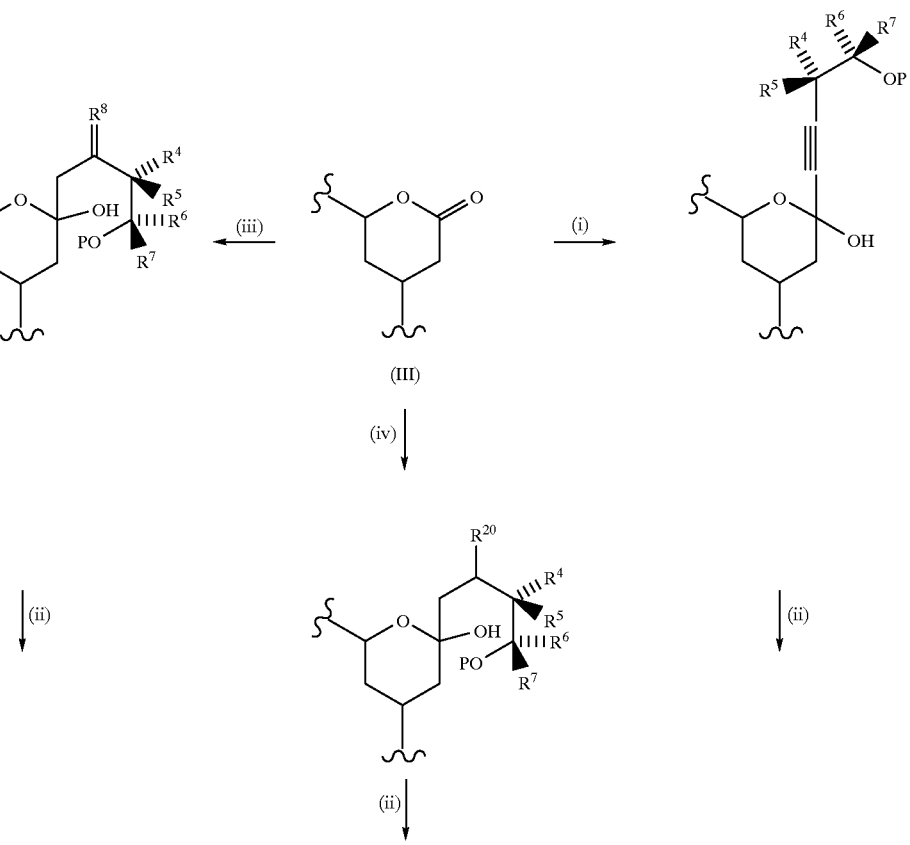

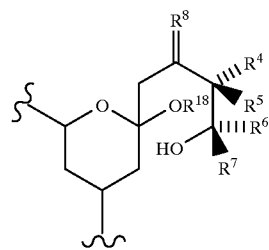 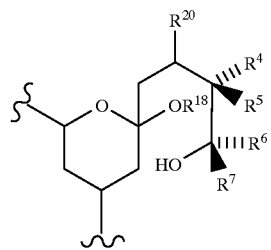 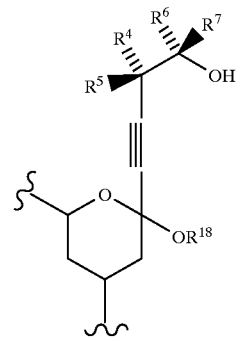

Notes (i) MC≡C-CR⁴R⁵-CR⁶R⁷OP where M is a metalating agent such as Li or BrMg and P is a protecting group eg an acid labile protecting group such as THP (tetrahydropyranyl)

(ii) $R^{18}OH/H^+$ (iii) $MCH_2CR^{8=}CR^4R^5\text{-}CR^6R^7OP$ (iv) $MCH_2CR^{20\text{-}}CR^4R^5\text{-}CR^6R^7OP$ Compounds of formula (III) can be prepared as described in EP-A-O 319 142 (U.S. Ser. No. 265,509) by cleaving the 21–22 carbon-carbon bond of a precursor having a hydroxy substituent on C22, such as compounds of formulae (A), (B), (C) and (D).

Those skilled in the art will appreciate that the process of the invention can be applied to essentially any milbemycin or avermectin having an optionally protected hydroxy (or oxo or oxime) group present at the C22 position. Furthermore, the compounds of formulae (I) and (III) can be further modified using techniques which are in themselves well known in the art and are described in, for example, Natural Products Reports 3 (2) [1986]87 et seq. and Macrolide Antibiotics [1984] Ch. 14, 553 et seq. Thus, a broad aspect of the invention provides any milbemycin or avermectin of partial formula (i) hereinbelow, as well as a process for its preparation which comprises (hydrating and) cyclizing a milbemycin or avermectin of partial formula (ii), (iii) or (iv) hereinbelow:

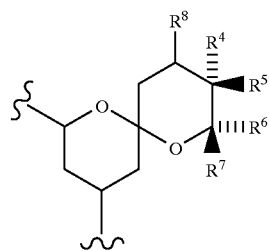

(i)

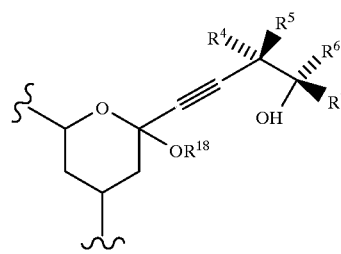

(ii)

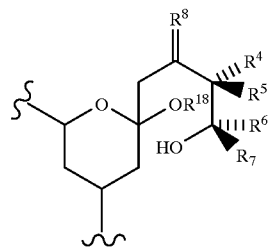

(iii)

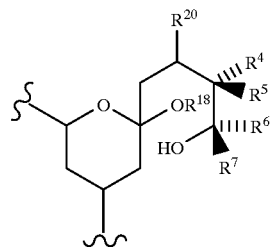

(iv)

wherein $R^4$ to $R^8$ and $R^{18}$ have the values set out above; and/or, optionally, converting a compound of formula (i) to a different compound of formula (i) as set out hereinabove.

A further broad aspect of the invention provides a novel process for the preparation of milbemycins and avermectins of partial formula (v):

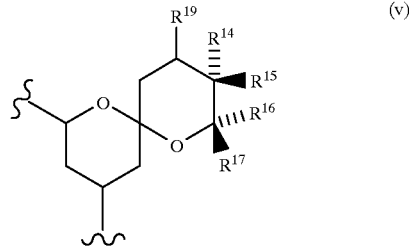
(v)

wherein $R^{14}$ to $R^{17}$ are the same or different and each is selected from hydrogen and an organic radical; and $R^{19}$ is optionally protected hydroxy, oxo, or an optionally substituted amino or imino group such as optionally O-substituted oxyimino, or optionally N-substituted hydrazone or semicarbazone, which process comprises (hydrating and) cyclizing a corresponding milbomycin or avermectin of partial formula (vi), (vii) or (viii)

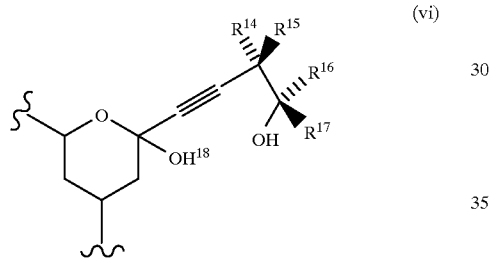
(vi)

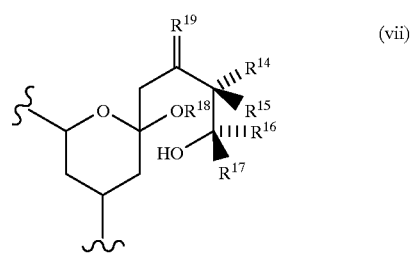
(vii)

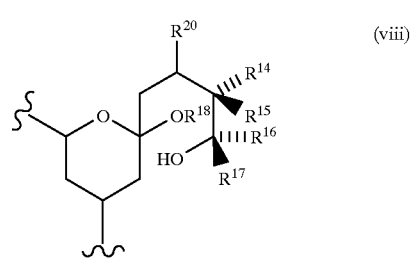
(viii)

wherein $R^{14}$ to $R^{19}$ have the values set out above; and/or, optionally, consorting a compound of formula (V) to a different compound of formula (v) az set out hereinabove.

Acetylenic precursors of structure $HC\!-\!C\!-\!CR^4R^5\!-\!CR^6R^7OP$ may be prepared using the procedures described in EP-A-O 353 959 (U.S. Ser. No. 387,351).

Precursors of structure $MCH_2CR^8\!-\!CR^4R^5\!-\!CR^6R^7OP$ may be prepared by treating a compound of formula $CH_3CR^8\!-\!C^4R^5\!-\!CR^6R^7OP$ with a suitable metalating agent such as n-butyllithium in an inert solvent such as THF at low temperatures eg about $-70°$ C.

Precursors of structure $MCH_2C(OP)_2\!-\!CR^4R^5\!-\!CR^6R^7OP$ may be prepared using procedures analogous to those described in EP-A-O 353 959.

The following Examples illustrate the present invention. VS 47709 its the compound of formula (III) wherein $R^1$ and $R^3$ are both hydrogen and $R^2$ is methoxy. VS 48927 is the compound of formula (III) wherein $R^1$ and $R^3$ are both hydrogqn and $R^2$ is hydroxy protected with TBDMS. "Milbemycin X" represents the following structure:

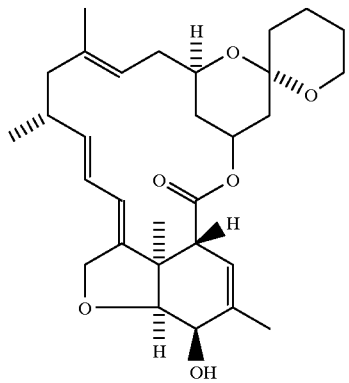

EXAMPLE 1

(24R, 25S)-24-methyl-23-oxo-25-phenyl-milbemycin X.

A mixture of (3S, 4S)-3-methyl-4-phenyl-4-(t-butyldimethylsilyloxy)-1-butyne (2.36 g, 8.6 mmol) and dry THF (40 ml) was cooled to $-78°$ C. under nitrogen. 1.6M-Butyllithium in hexane (4.7 ml, 7.5 mmol) was added dropwise with stirring and stirring continued at $-78°$ C. (2 h). A solution of VS 48927 prepared as described in Examples 1 to 3 of EP-A-0 319 142 (U.S. Ser. No. 265, 509) (1.2 g, 2.2 mmol) in dry THF (4 ml) was rapidly added and the mixture stirred at $-78°$ C. (20 min). A solution of acetic acid (1.5 ml) in THF (10 ml) was cooled to $-78°$ C. and then rapidly added to the reaction mixture. After warming to R.T. IM-ammonium chloride solution (100 ml) was added and the mixture extracted with ether (3×40 ml). The combined ethereal extracts were washed with saturated sodium bicarbonate solution (40 ml), dried ($MgSO_4$) and evaporated.

The residue was dissolved in methanol (20 ml). Toluene-4-sulphonic acid (ca 200 mg) was added and the mixture stirred at R.T. (17 h), treated with water, (100 ml) and extracted with ether (3×40 ml). The combined ethereal extracts were washed with saturated sodium bicarbonate solution (40 ml), dried ($MgSO_4$) and evaporated. The product was purified by silica gel column chromatography with light petroleum (b.p. 40–60° C.)-ethyl acetate, 3:2 as eluant (yield 0.96 g).

A portion of the above intermediate product (197 mg, 0.32 mmol) was dissolved in methanol (6 ml). A solution of mercuric oxide (7 mg, 0.03 mmol) in a mixture of concentrated sulphuric acid (0.1 ml) and water (3 ml) was added.

The reaction mixture was stirred at R.T. (3 h), treated with water (50 ml) and then extracted with dichloromethane (3×20 ml).

The combined dichloromethane extracts were dried (MgSO$_4$) and evaporated. The residue was fractionated by silica gel column chromatography with light petroleum (b.p. 40–60° C.)-ethyl acetate, 2:1 as eluant giving (24R,25S)-24-methyl-23-oxo-25-phenyl-milbemycin X (125 mg). $^{13}$C n.m.r. (270 MHz; CDCl$_3$) included δ 205.70, 139.20, 128.53, 128.35, 127.50, 40.45, and 9.29 ppm.

EXAMPLE 2

(24S, 25S)-24-methyl-23-methoxyimino-25-phenyl-milbemycin X.

(24R, 25S)-24-methyl-23-oxo-25-phenyl-milbemycin X (203 mg, 0.34 mmol) was dissolved in methanol (20 ml). A solution of methoxylamine hydrochloride (204 mg, 2.43 mmol) in water (4 ml was added and the mixture stirred at R.T. (4 h). The bulk of the methanol was evaporated and the residue treated with water (50 ml) and then extracted with dichloromethane (3×20 ml). The combined dichloromethane extracts were dried (MgSO$_4$) and evaporated. The residue was fractionated by silica gel column chromatography with light petroleum (b.p. 40–60° C.)-etlyl acetate, 2:1 as eluant giving (24S, 25S)-24-methyl-23-methoxyimino-25-phenyl-milbemycin x as a single isomer. $^{13}$C n.m.t. (270 MHz; CDCl$_3$) included δ 155.43, 139.37, 128.32, 128.26, 127.61, 61.40, 40.63, and 11.01 ppm.

The following compounds of formula (I), wherein R$_1$=R$^3$=H, were prepared using the methods of Examples 1 and 2. Throughout the Examples, tile acetylenic precursors of formula HC═C—CR$^4$R$^5$—CR$^6$R$^7$OP were prepared using the routes described in EP-A-O 353 959 (U.S. Ser. No. 387, 351):

EXAMPLE 2A

Treatment of a methanolic solution of the title compound with 2M HCl for 16 h gave a small amount of the Z isomer which was separated from the E isomer by prep tic (SiO$_2$ hexane/ethyl acetate (2;1).

TABLE V

| Ex. No | Prep. as per Ex. No | R$^2$ | R$^7$ | R$^4$ | R$^6$ | R$^5$ | R$^8$ | Acetylenic Precursor Protecting group P | Route of preparation |
|---|---|---|---|---|---|---|---|---|---|
| 1 | 1 | OH | C$_6$H$_5$ | CH$_3$ | H | H | ═O | TBDMS | A and B |
| 2 | 2 | OH | C$_6$H$_5$ | CH$_3$ | H | H | ═N-OCH$_3$ (E isomer) | TBDMS | A and B |
| 3 | see below | OH | t-C$_4$H$_9$ | H | H | H | ═O | TES TBDMS | A and B |
| 4 | 1 | OCH$_3$ | | 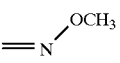 | H | H | ═O | TBDMS | B |
| 5 | 1 | OH | |  | H | H | ═O | TBDMS | B |
| 6 | see below | OH | t-C$_4$H$_9$ | H | H | H | ═N-OCH$_3$ (two isomers) | TBDMS | A and B |
| 7 | 2 | OH | |  | H | H | ═N-OMe (E isomer) | TBDMS | B |
| 8 | 1 | OH | Cyclo-C$_6$H$_{11}$ | CH$_3$ | H | H | ═O | TBDMS | A |
| 9 | 1 | OH | H | H | tert-C$_4$H$_9$ | H | ═O | TBDMS | A and B |
| 10 | 2 | OH | Cyclo-C$_6$H$_{11}$ | CH$_3$ | H | H | ═N-OCH$_3$ (E isomer) | TBDMS | A |

TABLE V-continued

| Ex. No | Prep. as per Ex. No | R2 | R7 | R4 | R6 | R5 | R8 | Protecting group P | Route of preparation |
|---|---|---|---|---|---|---|---|---|---|
| 11 | 2 | OH | t-C$_4$H$_9$ | CH$_3$ | H | H | =N-OCH$_3$ (E isomer) | TBDMS | A |
| 12 | 1 | OH | t-C$_4$H$_9$ | CH$_3$ | H | H | =O | TMS | A |
| 13 | 1 | OH | adamantyl | H | H | H | =O | TES | A |
| 14 | 6 | OH | adamantyl | H | H | H | =N-OCH$_3$ (E isomer) | TES | A |
| 15 | 6 | OH | adamantyl | H | H | H | =N-OCH$_3$ (Z isomer) | TES | A |
| 16 | 2 | OH | C$_6$H$_5$ | CH$_3$ | H | H | =N-NH-CONH$_2$ (E isomer) | TBDMS | A and B |
| 17 | 2 | OH | Cyclo-C$_6$H$_{11}$ | C$_2$H$_5$ | H | H | =N-OCH$_3$ (E isomer) | TBDMS | A |
| 18 | 2 | OH | C$_6$H$_5$ | n-C$_4$H$_9$ | H | H | =N-OCH$_3$ (E isomer) | TBDMS | A |
| 19 | 1 | OH | 4-CH$_3$.C$_6$H$_4$ | H | H | H | =O | TBDMS | A |
| 20 | 6 | OH | 4-CH$_3$.C$_6$H$_4$ | H | H | H | =N-OCH$_3$ (E isomer) | TBDMS | A |
| 21 | 6 | OH | 4-CH$_3$.C$_6$H$_4$ | H | H | H | =N-OCH$_3$ (Z isomer) | TBDMS | A |
| 22 | 2 | OH | H | H | Cyclo-C$_6$H$_{11}$ | CH$_3$ | =N-OCH$_3$ (E isomer) | TBDMS | B |
| 23 | 1 | OH | H | H | H | H | =O | TBDMS | Commercial Compound |
| 24 | 1 | OH | Cyclo-C$_6$H$_{11}$ | H | H | H | =O | TBDMS | A |

TABLE V-continued

| Ex. No | Prep. as per Ex. No | $R^2$ | $R^7$ | $R^4$ | $R^6$ | $R^5$ | $R^8$ | Protecting group P | Route of preparation |
|---|---|---|---|---|---|---|---|---|---|
| 25 | 6 | OH | Cyclo-$C_6H_{11}$ | H | H | H | =N-O$CH_3$, E isomer | TBDMS | A |
| 26 | 6 | OH | Cyclo-$C_6H_{11}$ | H | H | H | =N-O$CH_3$, Z isomer | TBDMS | A |
| 27 | 1 | OH | 1,1-dimethylcyclohexyl | H | H | H | =O | TES | A |
| 28 | 6 | OH | 2,2-dimethylpentyl | H | H | H | =N-O$CH_3$, E isomer | TES | A |
| 29 | 2 | OH | H | H | H | H | =N-O$CH_3$, E:Z 1:1 mixture | TBDMS | Commercial Compound |
| 30 | 1 | OH | 2,2-dimethylpentyl | H | H | H | =O | TES | A |
| 31 | 6 | OH | 2,2-dimethylpentyl | H | H | H | =N-O$CH_3$, Z isomer | TES | A |
| 32 | 6 | OH | t-$C_4H_9$ | H | H | H | =N-O$CH_2C_6H_4NO_2$, E isomer | TES | B |
| 33 | 6 | OH | t-$C_4H_9$ | H | H | H | =N-O$CH_2C_6H_4NO_2$, Z isomer | TES | B |
| 34 | 6 | OH | t-$C_4H_9$ | H | H | H | =N-O$C_2H_5$, E isomer | TES | B |
| 35 | 6 | OH | t-$C_4H_9$ | H | H | H | =N-O$C_2H_5$, Z isomer | TES | B |
| 36 | see below | OH | t-$C_4H_9$ | H | H | H | =N-O$C_4H_9$-t, E isomer | TES | B |

TABLE V-continued

| Ex. No | Prep. as per Ex. No | R² | R⁷ | R⁴ | R⁶ | R⁵ | R⁸ | Acetylenic Precursor Protecting group P | Route of preparation |
|---|---|---|---|---|---|---|---|---|---|
| 37 | see below | OH | t-C₄H₉ | H | H | H | 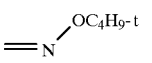<br>Z isomer | TES | B |
| 38 | 6 | OH | 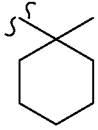 | H | H | H | 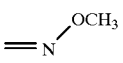<br>E + Z isomers | TES | A |
| 39 | 6 | OH | C₄H₉-t | CH₃ | H | H | 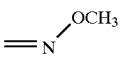<br>E + Z isomers | TMS | A |
| 40 | 6 | OH | n-C₆H₁₃ | H | H | H | 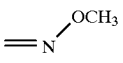<br>E isomer | TBDMS | A |
| 41 | 6 | OH | n-C₆H₁₃ | H | H | H | 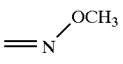<br>Z isomer | TBDMS | A |
| 42 | 2 | OH |  | H | H | H | 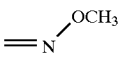<br>E isomer | TES | B |
| 43 | 6 | OH | C₄H₉-t | H | H | H | 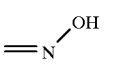<br>E + Z isomers | TES | B |
| 44 | 6 | OH | C₄H₉-t | H | H | H | 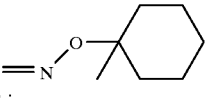<br>E isomer | TES | B |
| 45 | 6 | OH | C₄H₉-t | H | H | H | 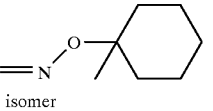<br>Z isomer | TES | B |
| 46 | see below | OH | C₄H₉-t | H | H | H | —OH<br>two epimers | — | — |
| 47 | 6 | OH | C₄H₉-t | H | H | H | 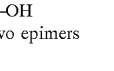<br>E + Z isomers | TES | B |
| 48 | 6 | OH | C₄H₉-t | H | H | H | 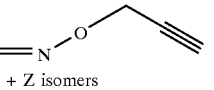<br>E + Z isomers | TES | B |

TABLE V-continued

| | Prep. as per | | | | | | | Acetylenic Precursor | |
|---|---|---|---|---|---|---|---|---|---|
| Ex. No | Ex. No | $R^2$ | $R^7$ | $R^4$ | $R^6$ | $R^5$ | $R^8$ | Protecting group P | Route of preparation |
| 49 | 6 | OH | $C_4H_9$-$\underline{t}$ | H | H | H | 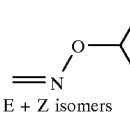 =N/O-CH(CH3)CH2- <br> E + Z isomers | TES | B |
| 50 | 2 | OH | $C_4H_9$-$\underline{t}$ | H | H | H | =N/OPh <br> E + Z mixture | TES | B |
| 51 | 2 | OH | $C_4H_9$-$\underline{t}$ | H | H | H | =N/NMe2 <br> E + Z mixture | TES | B |
| 52 | 6 | OH | 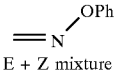 | | H | H | =O | TES | B |
| 53 | 54 | OH | $C_4H_9$-$\underline{t}$ | H | H | H | =N/OC(=O)NHC6H5 <br> E + Z isomers mixture | TES | B |
| 54 | see below | OH | $C_4H_9$-$\underline{t}$ | H | H | H | =N/OCH2OCH3 <br> E + Z isomers | TES | B |
| 55 | 6 | OH | $C_4H_9$-$\underline{t}$ | H | H | H | =N/OC(C2H5)3 <br> E + Z isomers | TES | B |
| 56 | see below | OH | $C_4H_9$-$\underline{t}$ | H | H | H | =N—CH2C(CH3)3 <br> E + Z isomers | TES | B |
| 57 | see below | OH | $C_4H_9$-$\underline{t}$ | H | H | H | H <br> —N—CH2C(CH3)3 <br> Two Epimers | TES | B |

EXAMPLE 3

23 Oxo-25(S)-t-butyl milbemycin x

To a solution of (4S)-5,5-dimethyl-4-triethylsilyloxy-1-hexyne (8.3 g, 33 mmol) in THF (100 ml) at −78° C. under a nitrogen atmosphere was added butyllithium (1.6M in hexane, 18.9 ml, 30 mmol) dropwise over a period of 5 mins. and the mixture stirred at −78° C. for a further 3 H. A solution of VS 48927 (4.8 g, 8.6 mmol) in THF (20 ml) was added to the mixture which was stirred at −78° C. for a further 15 mins. The reaction was quenched with a cold solution (−20° C.) of glacial acetic acid (10 ml) in THF (10 ml) and the mixture was then allowed to warm to 0° C. Brine (100 ml) was added and the mixture was extracted with ether (3×100 ml). The combined organic extracts were washed with water, dried (MgSO₄) and evaporated to an approximate volume of 50 ml. Methanol (50 ml) was added and the solution again evaporated to an approximate volume of 50 ml. 4-Toluenesulphonic acid (1 g) was added and the mixture stirred at 20° C. for 1 h.

Sodium bicarbonate (100 ml) was added to the mixture and the whole extracted with dichloromethane (3×100 ml). The combined organic extracts were washed with brine (100 ml), dried (MgSO₄) and evaporated. The residue was purified by column chromatography (silica eluted initially with dichloromethane and subsequently gradient eluted with 10–60% ethyl acetate in hexane) to afford the methylacetal (3.35 g, 66%).

This product (3.35 g 5.7 mmol) was dissolved in methanol (25 ml) and a solution of mercuric oxide (56 mg, 0.26 mmol) water (3.5 ml) and concentrated sulphuric acid (0.75 ml, 14 mmol) was added dropwise at 20° C. The mixture was stirred at 20° C., for 2 h., water was added and the mixture was extracted with dichlorormethane (3×100 ml). The combined organic layers were washed with sodium bicarbonate solution (100 ml), dried (MgSO₄) and evaporated to give the title ketone (3.2 g)) pure by nmr+tlc.

EXAMPLE 3A

23 Oxo-25(s)-t-butyl milbemycin X dimethyl acetal

Treatment of the ketone of example 3 with methanol and 4-toluenesulphonic acid for 24 h gave the title compound.

EXAMPLE 6

23-Oxo-25(S)-t-butyl milbemycin X (50 mg, 0.09 mmol) was dissolved in methanol (5 ml). A solution of methoxylamine hydrochloride (50 mg, 0.60 mmol) in water (2 ml) was added and the mixture stirred at room temperature (1 h). The reaction mixture was concentrated and then treated with water (30 ml) and extracted with ether (3×15 ml). the combined ethereal extracts were dried (MgSO$_4$) and evaporated. The 1:1 mixture* of Z and E oximes was separated by silica gel preparative thin layer chromatography with hexane—ethyl acetate, 1:1 as eluant.

* Ratio is dependent upon the pH of the reaction mixture.

The 23(Z)-methoxyimino-25(S)-t-butyl milbemycin X was obtained as a white solid (yield 16 mg). M/Z (FAB Na$^+$/Noba) 622 [MNa]$^+$ 50% (relative intensity). Hplc retention time=7.7 min.

The 23(E)-methoxyimino-25(S)-t-butyl milbemycin X was obtained as a white solid (yield 16 mg). M/Z (FAB Na$^+$/Noba) 622 [MNa]$^+$ 25% (relative intensity). Hplc retention time=7.9 min.

Hplc conditions: Dynamax C18 column (25 cm×4.6 mm id) eluted with methanol—water, 9:1 at 1 ml/min monitored at 245 nm.

EXAMPLES 36 and 37

23 (E and Z)-t-butyloxyimino -25 (S)-t-butyl milbemycin X

To a solution of 23-keto-25(S)-t-butyl milbemycin X (60 mg 0.1 mmol) and sodium acetate (300 mg, 2.2 mmol) in methanol (3 ml) was added 0-t-butylhydroxylamine hydrochloride (50 mg, 0.4 mmol). The mixture was stirred at 20° C. for 1 h., water (10 ml) was added and the whole mixture extracted with dichloromethane (3×15 ml). The combined organic extracts were washed with water, dried (MgSO$_4$) and evaporated to dryness. Purification by preparative t.l.c., (silica taper plate (Analtech®) eluted with ethyl acetate/hexane 2:5) yielded the title oximes as a 4:1 mixture of E:Z oxime isomers (54 mg). Treatment of a portion of this mixture (30 mg) with methanol (2 ml) and hydrochloric acid (1M, 0.2 ml) gave a 1:1 E:Z ratio of oxime isomers. The two isomers were separated by preparative t.l.c. (silica taperplate eluted four times with chloroform).

23(Z)-t-butyloxyimino-25(S)-t-butyl milbemycin X: tlc R$_f$=0.5 (Silica eluted three times with chloroform containing 1.5% ethanol) m/z (FAB Na$^+$/Noba) (relative intensity) 664 [MNa]$^+$ (95%).

23(E)-t-butyloxyimino-25(S)-t-butyl milbemycin X: tlc R$_f$=0.45 (Silica eluted three times with chloroform containing 1.5% ethanol) m/z (FAB Na$^+$/Noba) (relative intensity) 664 [MNa]$^+$ (95%).

Hplc retention times: Dynamax 60A Silica column (25 cm×4.6 mm id) eluted with chloroform/methanol 99:1 at 1 ml/min monitored at 245 nm.

Retention time 23-Z isomer=14.2 min.
Retention time 23-E isomer=15.4 min.

EXAMPLE 46

23(R)-hydroxy-25(S)-t-butyl-milbemycin X and 23 (S) epimer

To a solution of 5-O-triisopropylsilyl-23-oxo-25(S)-t-butyl milbemycin X (50 mg, 0 069 mmol) (obtainable from the compound of Example 3) in methanol (5 ml) was added sodium borohydride (10 mg, 0.26 mmol) and the mixture was stirred at 20° C. for 30 mins. Brine (25 ml) was added and the mixture was extracted with ether (3×10 ml). The combined ether extracts were washed with water, dried (MgSO$_4$) and evaporated to dryness. The residue was dissolved in methanol (3 ml), 4-toluenesulphonic acid (5 mg) added and the mixture was stirred at 20° C. for 16 h. Saturated sodium bicarbonate solution (10 ml) was added and the mixture was extracted with dichloromethane (3×10 ml). The combined organic extracts were washed with water (10 ml), dried (MgSO$_4$) and evaporated to give the crude R and S alcohols. The two products were separated and purified using preparative t.l.c. taper plates. (Silica eluted with ethyl acetate/hexane 2:5)

1) 23(R)-hydroxy-25(S)-t-butyl-milbemycin X (20 mg) t.l.c. R$_f$=0.45 (SiO$_2$/Ethyl acetate/hexane 1:1); m/z (FAB Na$^+$/Noba)(relative intensity) 595 [MNa]$^+$ (15%).

2) 23(S)-hydroxy-25(S)-t-butyl-milbemycin X (9 mg) t.l.c. R$_f$=0.35 (SiO$_2$/Ethyl acetate/hexane 1:1) m/z(FAB Na$^+$/Noba)(relative intensity) 595 [MNa]$^+$ (10%).

EXAMPLE 54

(a) 5-Acetoxy-23-keto-25(S)-t-butyl-milbemycin X 23-keto-25(S)-t-butyl milbemycin x was acetylated with acetic anhydride in pyridine in the normal manner. The resultant 5-acetoxy-23-keto-25(S)-t-butyl milbemycin X was purified by silica gel column chromatography with hexane-ethylacetate, 2:1 as eluant.

b) 5-Acetoxy-23-hydroxyimino-25(S)-t-butyl milbemycin X

A solution of hydroxylamine hydrochloride (0.34 g, 4.9 mmol) in water (5 ml) was added to a mixture of 5-acetoxy-23-keto-25(S)-t-butyl milbemycin X (1.0 g, 1.6 mmol), sodium acetate (0.78 g, 5.7 mmol) and methanol (30 ml). The mixture was stirred at R.T. (45 min). Water (100 ml) was added and the mixture extracted with ether (3×70 ml). The combined ethereal extracts were dried (MgSO$_4$) and evaporated giving 5-acetoxy-23-hydroxyimino-25(S)-t-butyl milbemycin X (0.9 g; 88%).

(c) 23-(E and z)-methoxymethoxyimino-25($\epsilon$) t-butyl milbemycin X

3M-Methyl magnesium iodide (0.4 ml. 1.2 mmol) was added dropwise to a stirred solution of 5-acetoxy-23-hydroxyimino-25(S)-t-butyl milbemycin X (368 mg, 0.6 mmol) in HMPA (10 ml) under a nitrogen atmosphere. After 5 min. bromomethyl methyl ether (0.07 ml, 0.8 mmol) was added and the mixture stirred at R.T. (1 h). Ether (40 ml) and 0.5M-hydrochloric acid (50 ml) were added to the reaction mixture. The organic layer was washed with 0.5M-hydrochloric acid, water, saturated sodium chloride solution, dried (MgSO$_4$) and evaporated.

The residue, methanol (10 ml) and 1M-sodium hydroxide (0.5 ml) were stirred in ice (2 h). Ethyl acetate (40 ml) was added and the mixture washed with 0.5M-hydrochloric acid, water, dried (MgSO$_4$) and evaporated. Purification by silica gel column chromatography with hexane-ethyl acetate, 2:1 afforded a mixture of 23-(E and Z)-methoxymethoxyimino-25(S)-t-butyl milbemycin X. The E and Z isomers were separated by preparative t.l.c. with hexane—ethyl acetate, 1:1 as eluant.

EXAMPLE 56

23-(2,2-dimethylpropylimino)-25(S)-t-butyl milbemycin X

A solution of 23-keto-25(S)-t-butyl milbemycin X (60 mg, 0.1 mmol) and 2,2-dimethylpropylamine (0.2 ml) in dry tetrahydrofuran (5 ml) was stirred at 70° C. in the presence of p-toluenesulphonic acid monohydrate (trace) and 4A molecular sieves for 16 h. The cooled solution was filtered and concentrated to a brown solid. Separation by column chromatography on silica eluting with ethyl acetate:hexane (1:1 v/v) gave the title compound as a solid. Mass spectrum FAB (NoBA/Na) m/z 662 (MNa+).

EXAMPLE 57

23-(2,2-dimethylpropylamino)-25(S)-t-butyl milbemycin X

To a solution of 23-keto-25(S)-t-butyl milbemycin X (63 mg, 0.11 mmol) and 2,2-dimethylpropylamine (0.2 ml) in methanol (2 ml) at room temperature was added sodium cyanoborohydride (7 mg, 0.11 mmol) and 2N aqueous hydrochloric acid (0.1 ml). The solution was stirred for 18 h poured into water and extracted with ethyl acetate. The organic phase was dried (MgSO$_4$) and evaporated to a white solid. Separation by thin layer chromatography on silica eluting with ethyl acetate:hexane (7:3 v/v) gave both the 23(R)- and 23(S)-products. Mass spectrum FAB (NoBA-Na) m/z 664 (MNa+) for both products.

Reference Example (preparation of acetylenic precursor for Example 3)

5,5-dimethyl-1-hexyn-4-ol 3,3-Dimethyl-1,2-epoxybutane (10 g, 100 mmol) was slowly added (over 30 min) to a stirred mixture of lithium acetylide ethylene diamine complex (90%, 15.3 g, 150 mmol) and dry DMSO (40 ml) under a nitrogen atmosphere. The temperature was maintained at 10–15° C. throughout the addition and the reaction stirred at approx. 15° C. for a further 3 h. The mixture was cooled in ice and cautiously treated with ice cold water (200 ml). The dark coloured solution was extracted with ether (3×50 ml) and the ether extracts dried (MgSO$_4$) and evaporated. The residue was purified by column chromatography (silica eluted with 40–60° PE/ether 9:1) to yield the alcohol (8.9 g., 71%).

Resolution of 5,5-dimethyl-1-hexyn-4-ol
(a) Preparation of (S)-O-acetylmandelate A solution of (R,S)-5,5-dimethyl-1-hexyn-4-ol (15 g, 119 mmol), (S)-O-acetylmandelic acid (23 g, 119 mmol) and 4-dimethylaminopyridine (1.45 g 11.9 mmol) in dichloromethane (300 ml) was cooled in ice and DCC (24.5 g 119 mmole) added over a period of 45 mins. The resulting mixture was stirred at room temperature for 1 h. Tlc (Silica eluted with 20% ether in hexane) showed the reaction to be complete. The mixture was filtered and the filtrate washed successively with dilute hydrochloric acid, dilute sodium bicarbonate solution and brine. The extract was dried (MgSO$_4$) and evaporated. The resulting oil was dissolved in hexane (50 ml) and left to crystallise. Crystals of the (S)-O-acetylmandelate ester of (S)-5,5-dimethyl-1-hexyn-4-ol (13 g 72%) were recovered by filtration and washed with a small volume of hexane.
b) Hydrolysis of (S)-O-acetylmandelate The (S)-O-acetylmandelate ester (13 g) was dissolved in methanol (200 ml) and treated with a solution of potassium carbonate (30 g) in water (50 ml). The mixture was stirred at room temperature for 5 days after which time tlc (silica eluted with 20% ether in hexane) indicated that the reaction was complete. Water (250 ml) was added and the mixture extracted with hexane. The hexane extract was washed with water and cautiously evaporated to remove most of the hexane. Purification of the residue by column chromatography (silica eluted with Petrol (40–60°)/ether (5:1) yielded the pure (S)-alcohol (5.2 g 96%).

(S)-5,5-dimethyl-4-(triethylsilyloxy)-1-hexyne

A mixture of (S)-5,5-dimethyl-1-hexyn-4-ol (1.96 g 16 mmol), triethylamine (4.5 ml, 32 mmol) and dry dichloromethane (30 ml) was cooled to 0° C. under a nitrogen atmosphere. Triethylsilyl trifluoromethanesulphonate (5.4 ml, 24 mmol) was slowly added and the mixture stirred at 0° C. for a further 40 min. The mixture was treated with saturated sodium bicarbonate solution (60 ml) and the organic layer separated. The aqueous layer was extracted with dichloromethane (3×20 ml) and the combined dichloromethane extracts dried (MgSO$_4$) and evaporated. The residue was purified by column chromatorgaphy (silica eluted with Petroleum ether 40–60°) to yield the title compound 3.55 g (95%).

We claim:
1. A process for preparing a compound of formula (I)

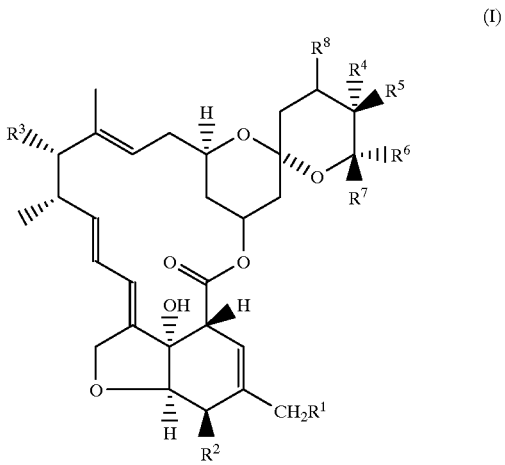

(I)

wherein $R^1$ is hydrogen or optionally protected hydroxy;

$R^2$ is alkoxy, optionally protected hydroxy, oxo, oximino, or oximino substituted by an organic radical;

$R^3$ is hydrogen, optionally protected hydroxy, or a group 4'-(α-L-oleandrosyl) -α-L-oleandrosyloxy or α-L-oleandrosyloxy wherein the terminal hydroxy group is optionally protected;

$R^4$, $R^5$, $R^6$, and $R^7$ are the same or different and each is hydrogen or an organic radical; and $R^8$ is amino, imino, amino substituted by an organic radical, imino substituted by an organic radical, optionally protected hydroxy, or oxo, the process comprising: (hydrating and) cyclizing a compound of formula (II), (IV), or (V)

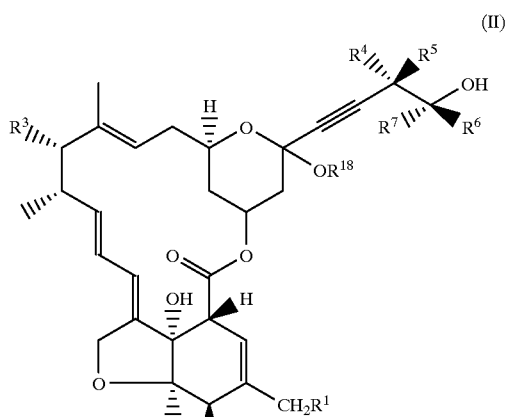
(II)

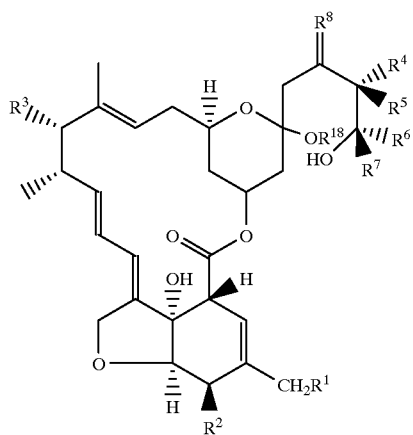
(IV)

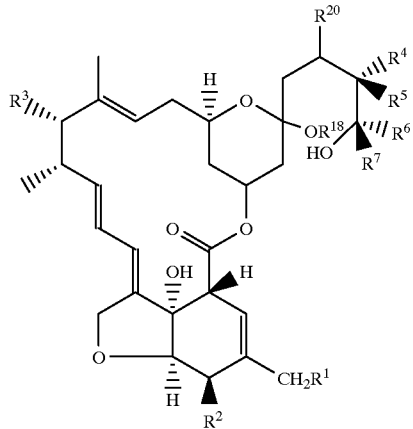
(V)

wherein $R^{18}$ is hydrogen or lower alkyl, and $R^{20}$ is optionally protected ketone.

2. A process for preparing a compound of formula (I):

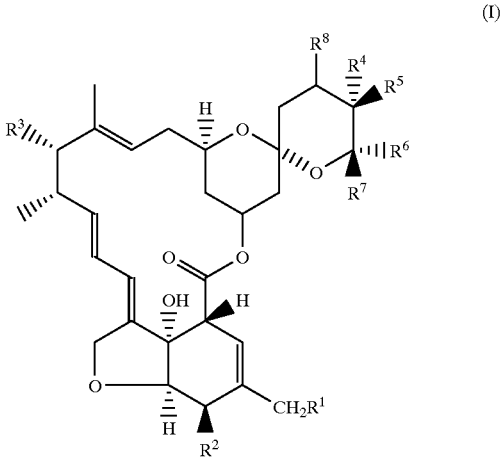
(I)

wherein $R^1$ is hydrogen or optionally protected hydroxy;

$R^2$ is alkoxy, optionally protected hydroxy, oxo, oximino, or oximino substituted by an organic radical;

$R^3$ is hydrogen, optionally protected hydroxy, or a group 4'-(α-L-oleandrosyl)-α-L-oleandrosyloxy or α-L-oleandrosyloxy wherein the terminal hydroxy group is optionally protected;

$R^4$, $R^5$, $R^6$, and $R^7$ are the same or different and each is hydrogen or an organic radical; and $R^8$ is amino, imino, amino substituted by an organic radical, imino substituted by an organic radical, optionally protected hydroxy, or oxo, which process comprises:

(a) treating a compound of formula (III)

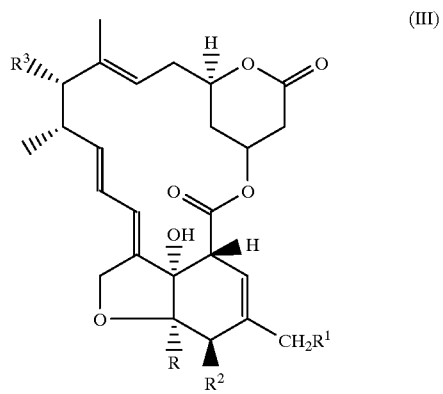
(III)

with a compound selected from the group consisting of MC≡C—$CR^4R^5$—$CR^6R^7OP$, $MCH_2CR^8$—$CR^4R^5$—$CR^6R^7OP$, and $MCH_2CR^{20}$—$CR^4R^5$—$CR^6R^7OP$, wherein M is a metalating agent, P is a protecting group, and $R^{20}$ is optionally protected ketone;

(b) treating the compound obtained from step (a) with an acid/$R^{18}$OH to obtain a compound of formula (II), (IV), or (V) as defined in claim 12; and (c) carrying out in-situ acid-catalyzed cyclization of the compound of formula (II), (IV), or (V) obtained in step (b).

3. A process according to claim 1, wherein $R^1$ and $R^3$ are hydrogen, $R^2$ is hydroxy, and $R^8$ is oxyimino substituted by an organic radical.

4. A process according t claim 1, wherein $R^1$ and $R^3$ are hydrogen, and $R^2$ and $R^4$ to $R^8$ inclusive are selected from among the values set forth in Table V of the specification.

5. A process according to claim 1, which process comprises: (a) hydrating and cyclizing a compound of formula (II), or cyclizing a compound of formula (IV) wherein $R^8$ is oxo, or cyclizing a compound of formula (V); and (b) treating the compound of formula (I) so obtained in step (a) with a substituted hydroxylamine to convert $R^8$ to an oxyimino group substituted by an organic radical.

* * * * *